United States Patent [19]

Elson

[11] 4,241,739

[45] Dec. 30, 1980

[54] VOLUME CALCULATOR FOR INCENTIVE SPIROMETER

[75] Inventor: Edward E. Elson, Anaheim, Calif.

[73] Assignee: C. R. Bard, Inc., Murray Hill, N.J.

[21] Appl. No.: 959,911

[22] Filed: Nov. 13, 1978

[51] Int. Cl.³ .............................................. A61B 5/08
[52] U.S. Cl. .................................. 128/725; 272/99; 73/861.55
[58] Field of Search ............................. 128/725–729, 128/716; 272/99; 73/194 E, 209, 239, 453

[56] References Cited

U.S. PATENT DOCUMENTS

| 3,224,270 | 12/1965 | Karol et al. | 73/209 |
|---|---|---|---|
| 3,559,638 | 2/1971 | Potter | 128/727 |
| 3,606,883 | 9/1971 | Poirier et al. | 128/725 |
| 3,608,546 | 9/1971 | Shinn | 128/725 |
| 3,699,560 | 10/1972 | Meunier et al. | 73/209 X |
| 3,754,546 | 8/1973 | Cooper | 128/727 |
| 3,894,433 | 7/1975 | Riester | 73/209 |
| 3,946,726 | 3/1976 | Pikul | 128/725 |
| 3,985,124 | 10/1976 | Coleman | 128/727 |
| 3,994,175 | 11/1976 | Yamaguchi et al. | 73/453 |
| 4,134,301 | 1/1979 | Erwin, Jr. | 73/453 |

Primary Examiner—Lee S. Cohen
Attorney, Agent, or Firm—Richard H. Zaitlen

[57] ABSTRACT

An electronic device for use in conjunction with a spirometer for measuring the time interval during which a minimum predetermined air flow is maintained through the spirometer and for calculating the minimum total volume of air flowing through the spirometer during that interval of time and for automatically providing other related information to the patient and therapist using the spirometer.

24 Claims, 12 Drawing Figures

VOLUME CALCULATOR FOR INCENTIVE SPIROMETER

BACKGROUND OF THE INVENTION

1. Field of the Invention

The invention relates to devices for measuring the volume of air inspired by patients as part of a post operative respiratory exercise program, and more particularly to electronic devices for performing such measurements.

2. Prior Art

The use of incentive spirometers to encourage the post operative patient to fill his lungs completely has been proven to reduce the incidence of respiratory complications following surgery.

The incentive spirometers presently available fall into two categories, disposable and permanent with disposable elements. The disposable units are left with the patient during the course of his stay in the hospital and he is encouraged to inhale on it to fully inflate his lungs and gradually regain his preoperative lung capacity. A typical patient will be told to inhale deeply ten times an hour and with gradually increasing inspired volumes and flow rates until his performance matches at least his preoperative performance.

The permanent or reusable units, normally costing several hundreds of dollars each, incorporate a disposable element which may be a flow sensor or a volume canister and are used with a single patient at a time. When treatment is provided to a patient, the permanent part is provided with a new disposable element for each individual patient's use. Thus, one limitation of presently available permanent devices is that they either must be left with a single patient for his use throughout the day, thereby requiring a hospital to maintain a large inventory of expensive devices, or the devices must be moved from patient to patient thereby depriving the patient of the device until his turn comes again.

Spirometers may be constructed somewhat similar to the spirometers disclosed in U.S. Pat. Nos. 4,114,607 and 4,114,608.

The preferred embodiment of the present invention is particularly intended to operate in conjunction with the incentive spirometer which is the subject of U.S. Patent Application Ser. No. 739,271 filed Nov. 5, 1976.

These spirometers provide a mechanism to direct a patient to inhale air through a passageway having a flow regulator. Inhalation at a preset flow rate causes a visible indicator, such as a ball to rise to the top of a tube. A therapist may set up a program of respiratory exercise which calls for the patient to raise the ball to the top of the tube and hold it there for a specified time. The air flow regulator can be set to require various minimum flow rates for raising the ball to the top. The patient may be required to achieve the specified flow rate and hold the ball at the top of the tube for a specified time, a number of times per day. This type of program guarantees a certain minimum respiratory exercise.

In order to use these devices it is necessary for the patient, or therapist, to keep records by means of a pencil and paper and a stopwatch. Notations are made of the number of attempts made by the patient to achieve the required flow rate for the specified time, and of the number of successful attempts. To determine the volume of air inhaled on a particular attempt, the duration of time for which the ball remains at the top of the tube must be measured, e.g., by a stopwatch. Knowing the flow rate for which the regulator valve is set and the measured time, reference may then be made to charts to determine the volume of air inhaled, or the flow rate in cubic centimeters per second may be multiplied by the time in seconds; e.g., by hand.

The use of such devices is somewhat inconvenient in that either the patient must be supplied with a stopwatch and keep his own records, or a therapist must be present to time and make records whenever the patient performs an attempt to raise the ball.

The presence of a therapist may also be required to insure that the spirometer is being properly used. For example, if a patient is lying in bed and using the spirometer he may place the spirometer on blankets or on his stomach. Most likely the spirometer will not be truly vertical. The most valid measurements of air flow are made when the spirometer is vertical. The further from vertical the less accurate are the measurements of effort required to raise the ball.

Various devices designed to measure flow rate of a medium are known to applicant, including: Le Maitre et al, U.S. Pat. Nos. 4,078,554; Hutchinson, 2,333,791; Cooper, 3,754,546; Sanctuary et al, 3,818,901; and Kozak et al, 3,922,525.

Le Maitre shows a fairly complex spirometric device adapted for connection to the exhalation branch of a respiratory piping system. The device is particularly applicable to controlled delivery repsirators and uses a pressure pickup to provide data used in calculating the exhaled volume of air. The device is directed more at monitoring artificial respiration of a patient rather than controlling a post operative lung exercise program. Thus, Le Maitre makes use of the measured minimum and maximum pressures and Boyle's law rather than detecting the presence of an indicator.

Hutchinson shows a photoelectric device for counting globules of liquid of a known size and converting the number of such globules passing through a given point to a flow rate of the liquid.

Cooper provides an incentive spirometer of the type discussed earlier where there is only an indication given that a certain minimum flow rate has been achieved. In Cooper this is indicated by the turning on of the light. No measurement of the total volume of air inhaled is provided.

Sanctuary et al show a rather complex circuit arrangement for analyzing expired respiratory gases and measuring them. The volume of expired air is digitally displayed by means of a rotating slotted disc assembly.

Kozak shows a bidirectional spirometer with a moving vane type air flow sensor, the revolutions of the vane being counted to provide a measure of air flow.

It is an object of the present invention to provide a means for measuring and monitoring a patient's post operative respiratory exercise which does not require the use of a stopwatch, reference to charts, or hand calculations to determine the volume of air inspired.

It is another object of the invention to provide such a means which can be operated by the patient without requiring the presence of another person such as a therapist to assist in the patient's exercise program.

It is still a further object of the present invention to provide a means for calculating the volume of air inspired by a patient and for determining whether the patient was successful in his attempt to inspire a volume equal to or greater than that called for by the exercise program determined by the therapist.

It is again an object of the present invention to provide a means for recording the number of times a patient successfully inspires a volume of air equal to or greater than that called for by the exercise program and for determining whether the number of such successful efforts is equal to the number of successful efforts required by the exercise program.

Another object of this invention is to indicate to the patient the length of time he is required to hold his breath after he has successfully inspired the required volume of air.

A further objective is to provide a device which will automatically sense that its angular displacement from the vertical exceeds a preset value and in that event inhibit operation of the device.

The device should further display, on demand, the largest inhalation volume in the current series of inhalations.

It is an object of the present invention to provide such a device as discussed above which is portable and capable of operating in conjunction with a separate and independently operable spirometer such that the present device may be taken from the patient without depriving the patient of his spirometer.

SUMMARY OF THE INVENTION

The device of the present invention comprises an energy beam and electronic circuitry mounted in a housing which is matably mountable upon a spirometer having a flow rate indicator such that when the indicator interrupts the energy beam the electronic circuitry is activated. The circuitry, which includes a microprocessor, accepts input data such as minimum flow rate required, total volume required, total number of successful efforts required, and length of time patient should hold his breath. The microprocessor measures the time that the energy beam is interrupted by the indicator and calculates the total volume of inspired air. If this volume meets or exceeds the volume required under the therapist's program, a successful effort is recorded. In addition, the device will display the volume of air the patient is expected to inhale, how many times he is expected to inhale this volume, how long he must hold his breath after each inhalation, how much air he has actually inhaled, the number of successful efforts made and the greatest volume of air the patient has inhaled in the current exercise series.

DETAILED DESCRIPTION OF THE PREFERRED EMBODIMENT

FIGS. 1 through 5 show how the device of the present invention is intended to function in conjunction with a spirometer. For convenience the device of the present invention may often be referred to herein as the counter. This designation should be distinguished from the discussion at a later point, wherein reference is made to an electronic processing device or counting device used as a timing means, which is contained within the microprocessor. The present invention comprises a counter 8, more particularly shown in FIG. 1. The counter comprises primarily two portions. The first portion is the main body 10, the second portion is the detector housing 12 which protrudes from the upper front portion of the main body 10. Immediately above the detector housing are two display windows, a left display window 14 and a right display window 16. In order that the data displayed within these windows is more easily readable, there is provided a light shield 17 which extends outward from the body 10 and reduces the amount of light striking the windows. The detector housing 12 is provided with a downward opening cavity designed for mating engagement with a spirometer 18 which permits the counter 8 to be removably and matably mounted upon the spirometer 18. The spirometer comprises a base 20, a vertically extending chamber 22 and, located within the chamber, a moveable indicator 24 which is free to rise to the top of the chamber 22 as a result of the air flow through the chamber. This indicator 24 may comprise a ball or other device which, for purposes of the preferred embodiment of the present invention, is not transparent to light. By inhaling through orifice 25, a patient will cause air to flow through chamber 22 which will cause the indicator 24 to rise within the chamber 22. When the rate of air flow inhaled by the patient is equal to or exceeds the flow rate setting of the regulator valve 26, the indicator 24 will be caused to rise to the top of the chamber 22, thus indicating that the patient has achieved an inhalation rate at least equal to the setting of the valve 26.

Figures 1, 2:
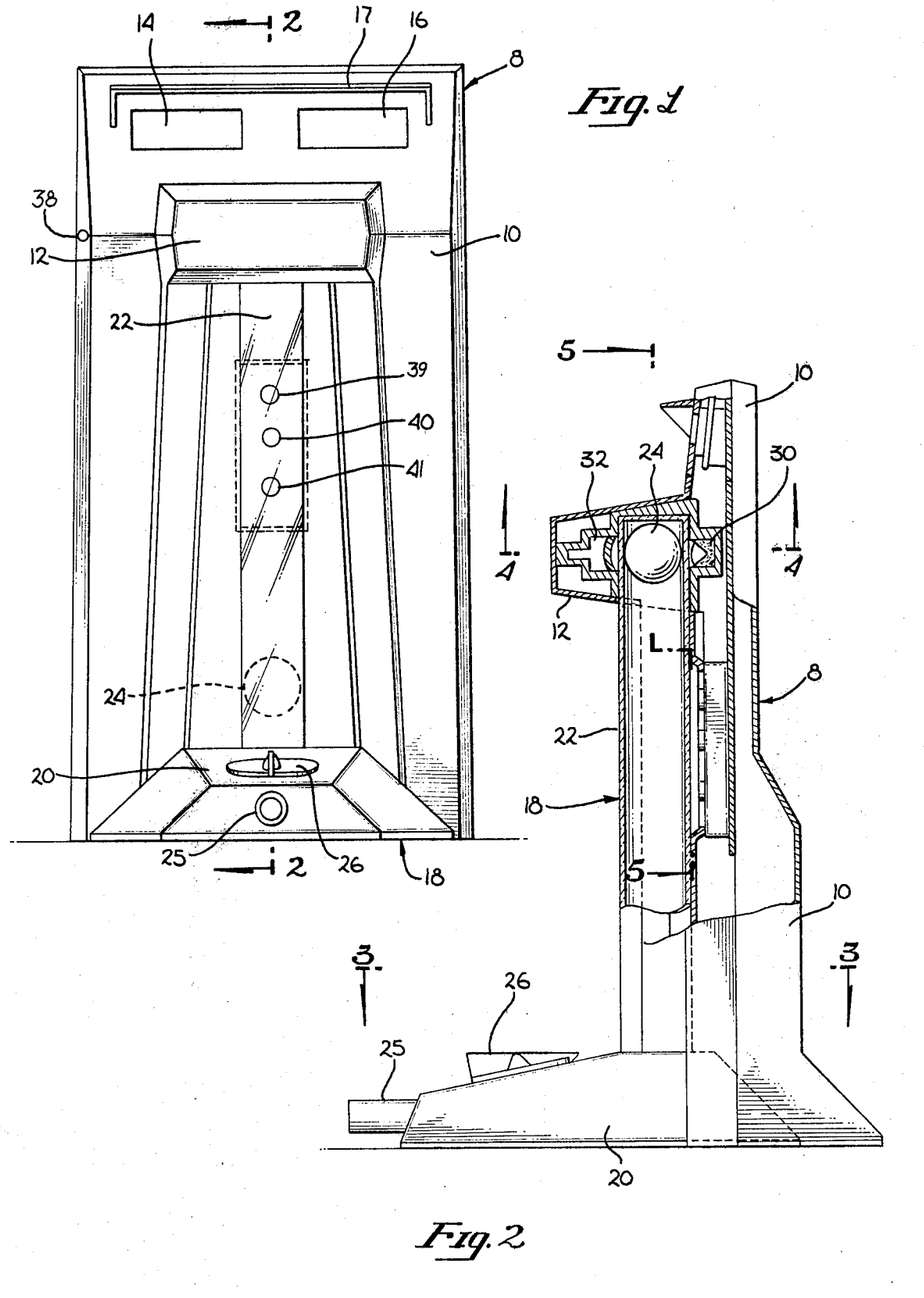
FIG. 1 is a front elevational view showing the device of the present invention mounted upon a spirometer.
FIG. 2 is a sectional view taken along the line 2—2 of FIG. 1.

As shown in FIG. 2 the detector housing 12 houses an energy source 30 and an energy detector 32. The energy source and energy detector communicate with one another by means of an energy beam traveling from the energy source to the energy detector 32. This is possible even though the counter 8 is mounted upon the sprirometers 18 because the spirometer chamber 22 is transparent to the particular type of energy transmitted by the energy source 30. It should be apparent to anyone skilled in the art that in place of the energy source 30 and energy detector 32, a proximity detector such as a magnetic sensor may be used. It is intended that the present invention be construed in the broadest sense to encompass any type of detector which provides an indication that an indicator device is present or absent at a particular location along the length of the chamber 22 of the spirometer. It is also contemplated that a plurality of such detectors may be employed at various locations along the length of the chamber 22 to detect the presence of the indicator at various locations as the indicator rises in the chamber.

When the inhalation rate of the patient through orifice 25 is equal to the minimum flow rate set on the regulator valve 26, the air flow through chamber 22 will cause the indicator 24 to rise to the top of the chamber 22 as shown in FIG. 2. Since the indicator 24 is chosen so as to not be transparent to the type of energy transmitted by the energy source 30, the presence of the indicator 24 will interrupt the beam of energy flowing from energy source 30 to the energy detector 32 resulting in a break in communication between the energy source and energy detector. This break in communication is of prime importance with respect to the present invention as will be more fully explained shortly.

Figure 3:
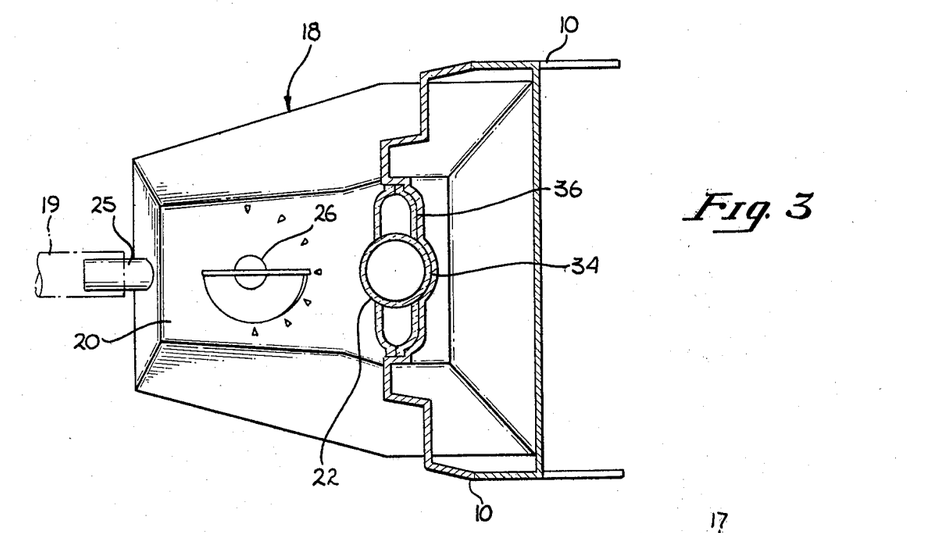
FIG. 3 is a sectional view taken along the line 3—3 of FIG. 2.

In order to facilitate the proper fitting of the counter 8 upon the spirometer 18, the body 10 of the counter is provided with channels 34 and 36 designed to match the contours of the chamber 22. This feature is most clearly illustrated in FIG. 3. These channels 34 and 36 extend along the vertical length of the counter 8 and the contours extend correspondingly along the vertical length of the chamber 22. FIG. 3 also affords a good illustration of the air flow regulator valve 26. In the particular spirometer illustrated in the present disclosure, the regulator valve 26 is merely a variable opening. The opening provides calibrated flow rates corresponding to the particular size of the opening when the indicator of the valve points to a particular calibration or dial setting. The calibration is generally in cubic centimeters per second and indicates the flow rate that must be achieved in order to raise the indicator to the top of the chamber 22. By inhaling through a long flexible tube 19 the patient will cause a flow of air to pass through orifice 25 and chamber 22. When the flow rate is equal to or exceeds the setting of the regulator valve 26, the indicator 24 will be raised to the top of the chamber 22.

Figure 4:
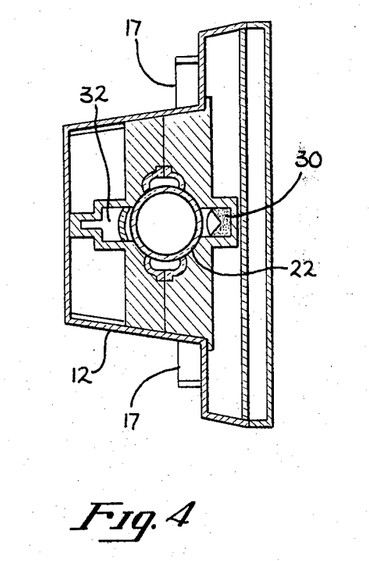
FIG. 4 is a sectional view taken along the line 4—4 of FIG. 2.

As shown in FIG. 4 the top of chamber 22 extends between the energy source 30 and the energy detector 32. When the indicator 24 rises to the top of the chamber 22 the indicator will interrupt the energy being transmitted between the energy source 30 and the energy receiver 32.

Figure 5:
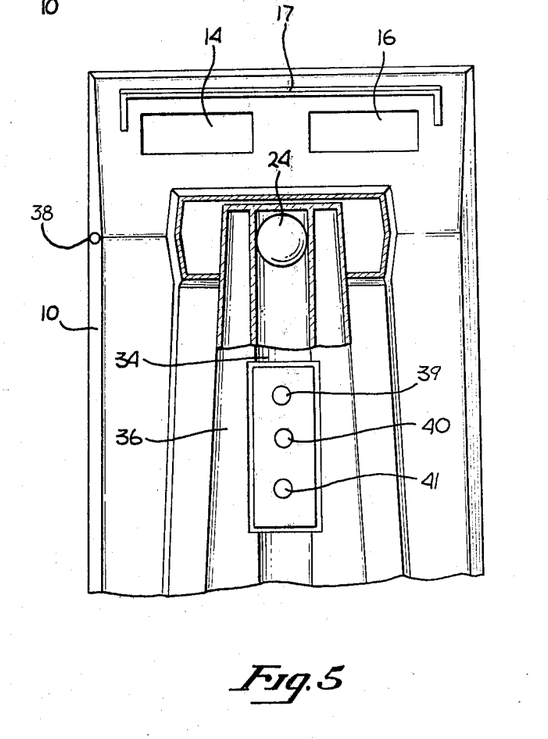
FIG. 5 is a partial sectional view taken along the line 5—5 of FIG. 2.

As discussed earlier, the present device is intended to be used in conjunction with a spirometer. A spirometer is a device which is used to insure that a postoperative patient is given an incentive for exercising his or her lungs to reduce the possibility of respiratory complications. It is generally the case that a hospital therapist will construct a program of such exercise to be followed by the patient. Such a program may call for the patient to achieve a certain minimum inhalation rate for a specified time, so that the patient will inhale a predetermined minimum volume of air. As part of the program, the patient may be required to inhale this volume, at the particular minimum flow rate, a predetermined number of times during the course of an hour or other prescribed time. Such a patient may also be required to hold the inhaled volume of air in his or her lungs for a specified time. It can thus be seen that there are a number of predetermined values which are of some importance in defining the program of respiratory exercise which the patient is to follow. Specifically, these parameters include the minimum flow rate to be achieved, the minimum total volume to be inhaled, the time that the patient is to hold the inhaled volume, and the number of times that the patient is to be required to inhale this predetermined minimum volume. The device of the present invention provides a means for entering the value of these parameters into a microprocessor which forms a part of the device of the present invention. The particular means by which such parameters are entered into the microprocessor comprise the register across switch 38, which is also used alone to display the data in a register, data entry switch 39, clear switch 40 and on/off switch 41. The location of these switches is as shown in FIG. 5. More specifically, these switches may be located and recessed within the channel 34. It should be expressly understood, however, that other locations are equally advantageous and may include location upon the exterior surface of the counter 8 as is the case for the register access switch 38. Once the therapist has determined the program of respiratory exercise which is appropriate for the particular postoperative patient, the above described parameters can be entered into the microprocessor by appropriate activation of the proper switch. When the device of the present invention is being operated by the therapist to enter the parameters described above, it is being operated in what will herein be referred to as the data entry mode. This mode of operation is schematically illustrated in FIG. 6.

The device of the present invention is preferably powered by battery power and is provided with an on-off switch 41. The sequence of operation for entering data into the microprocessor is as illustrated in steps 50 through 66 shown in FIG. 6. Step 50 calls for the therapist to activate the power on switch. In order to enter data into the microprocessor the therapist must access the proper memory register. Access to a particular memory register is gained by activation of the register access switch 38. Depression of switch 38 will permit access to the various memory registers in a pre-programmed sequence. Depression of switch 38 for the first time, will permit access to the "EFFORTS" register 118 (See FIG. 11). Data stored in the register will be displayed in windows 14 and 16. The next activation of the switch 38 will permit access to the "HIGHEST VOLUME" register 114. Similarly, successive activations of the switch 38 will permit access to the "FLOW RATE" (dial setting) register 106, the "VOLUME" register 112 and the "HOLD" register 120. The data contents of any particular register can be entered by accessing the particular register as described above and maintaining the register access switch 38 in the depressed condition while the data entry switch 39 is activated. By activating the data entry switch 39, the data contents of the particular register which is accessed are incremented in a predetermined sequence. If the "EFFORTS" register 118 is accessed, successive activation of the data entry switch 39 will increment the contents of the "EFFORTS" register 118 by one for each activation of the data entry switch 39. If the "FLOW RATE" register 106 is accessed, successive activation of the data entry switch 39 will increment the contents of the "FLOW RATE" register in steps corresponding to the calibrations on the regulator valve 26. Thus, when the "FLOW RATE" register is accessed and the register access switch 38 is held in the depressed condition, the successive activation of data entry switch 39 will increment the contents of the "FLOW RATE" register. This will continue until the value of 1,800 cubic centimeters per second is reached at which time the next activation of the data entry switch 39 will return the contents of the "FLOW RATE" register to the starting point of 145 cubic centimeters per second. Similarly, the contents of the various other registers can be changed incrementally by successive activation of the data entry switch 39 while the register access switch 38 is held in the depressed condition.

Figure 6:
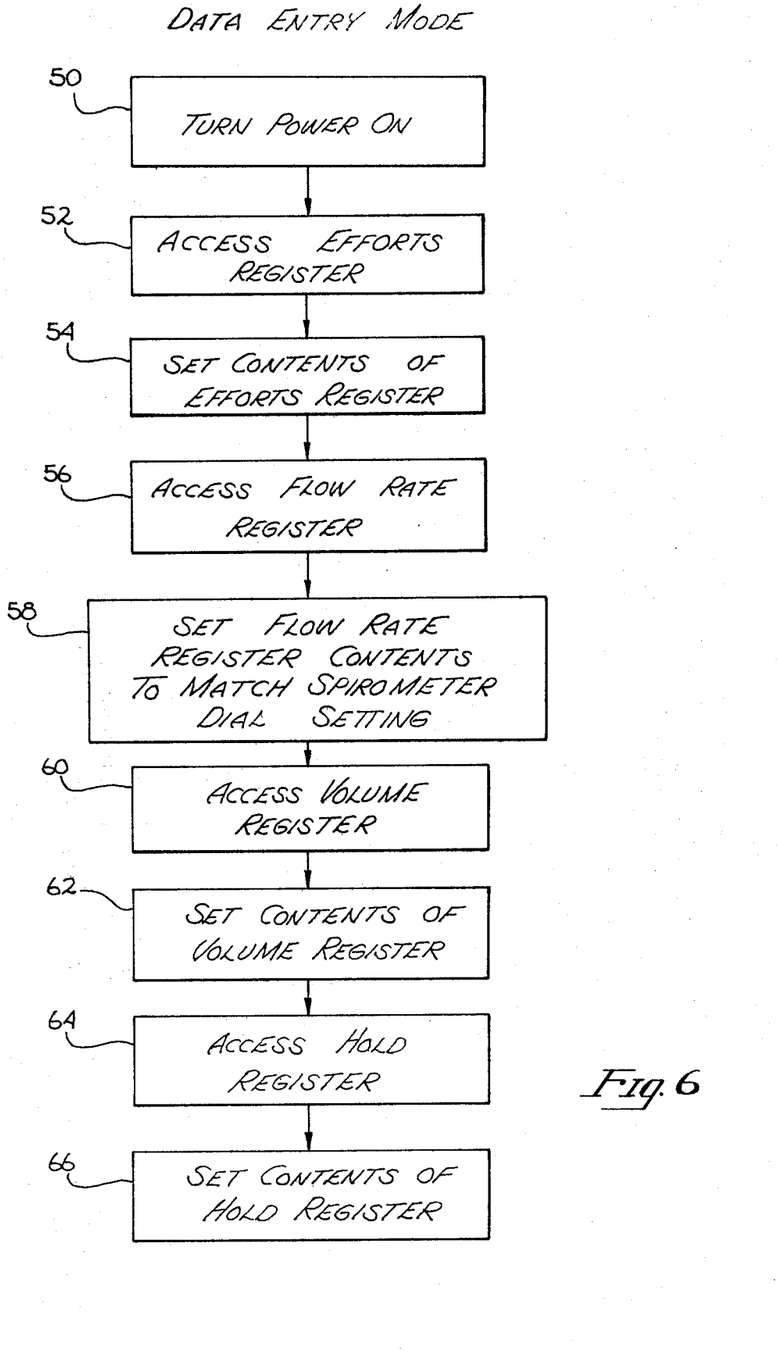
FIG. 6 is a flow chart of the data entry mode of operation of the invention.

The operation of the counter 8 in the data entry mode by the therapist, is thus aptly illustrated by FIG. 6. The therapist will first turn the device on as shown in step 50. The therapist will then access the "EFFORTS" register 118 as shown in step 52. This is accomplished by depression of the access switch 38 and while the switch is maintained in this depressed position, successive depression of the data entry switch 39 will increment and set the contents of the "EFFORTS" register, as shown in step 54. The contents of the "EFFORTS" register is incremented by one for each depression of the data entry switch 39. The contents of the "EFFORTS" register is set to the number of times that the therapist has determined it is desirable for the patient to inhale a predetermined minimum volume of air. The therapist will then release the register access switch 38 and depress register access switch 38 thereby gaining access to the "FLOW RATE" register 106 as shown in step 56. While the register access switch 38 is maintained in the depressed position, the data entry switch 39 is successively depressed thereby stepping the contents of the "FLOW RATE" register 106 until the contents of this register match the setting of the flow regulator valve 26 on the spirometer, as indicated in step 58. The therapist will then release and depress the register access switch 38 thereby gaining access to the "VOLUME" register as in step 60. With the register access switch 38 maintained in the depressed position, the therapist will successively depress the data entry switch 39. This successive depression of data entry switch 39 will step the contents of the "VOLUME" register in increments equal to the contents of the "FLOW RATE" register times one-half second. Thus, if the "FLOW RATE" register is set to 1440 cubic centimeters per second, the contents of the "VOLUME" register will be stepped by 720 cubic centimeters for each depression of the data entry switch 39 (see step 62). At this point the therapist will again release and depress the register access switch 38 and thereby gain access (see step 64) to the "HOLD" register 120. With the register access switch 38 maintained in the depressed position, the therapist will successively depress (see step 66) the data entry switch 39 and thereby increment the contents of the "HOLD" register by one-half second for each such successive depression of the data entry switch 39. The contents of the "HOLD" register indicated the number of seconds which the therapist desires the patient to hold his breath after he has inhaled the maximum volume of air that he is capable of inhaling. The contents of the "VOLUME" register is meant to be the minimum volume of air which the therapist desires the patient to inhale, in order to consider that particular inhalation attempt to be successful.

After the therapist has set the contents of the various registers as described above, the spirometer and the counter 8 are then left with the patient for his use in following the respiratory exercise program prescribed by the therapist. When used by the patient the device of the present invention will be referred to as operating in the patient operation mode. This mode of operation is graphically illustrated in FIG. 7.

Figure 7:
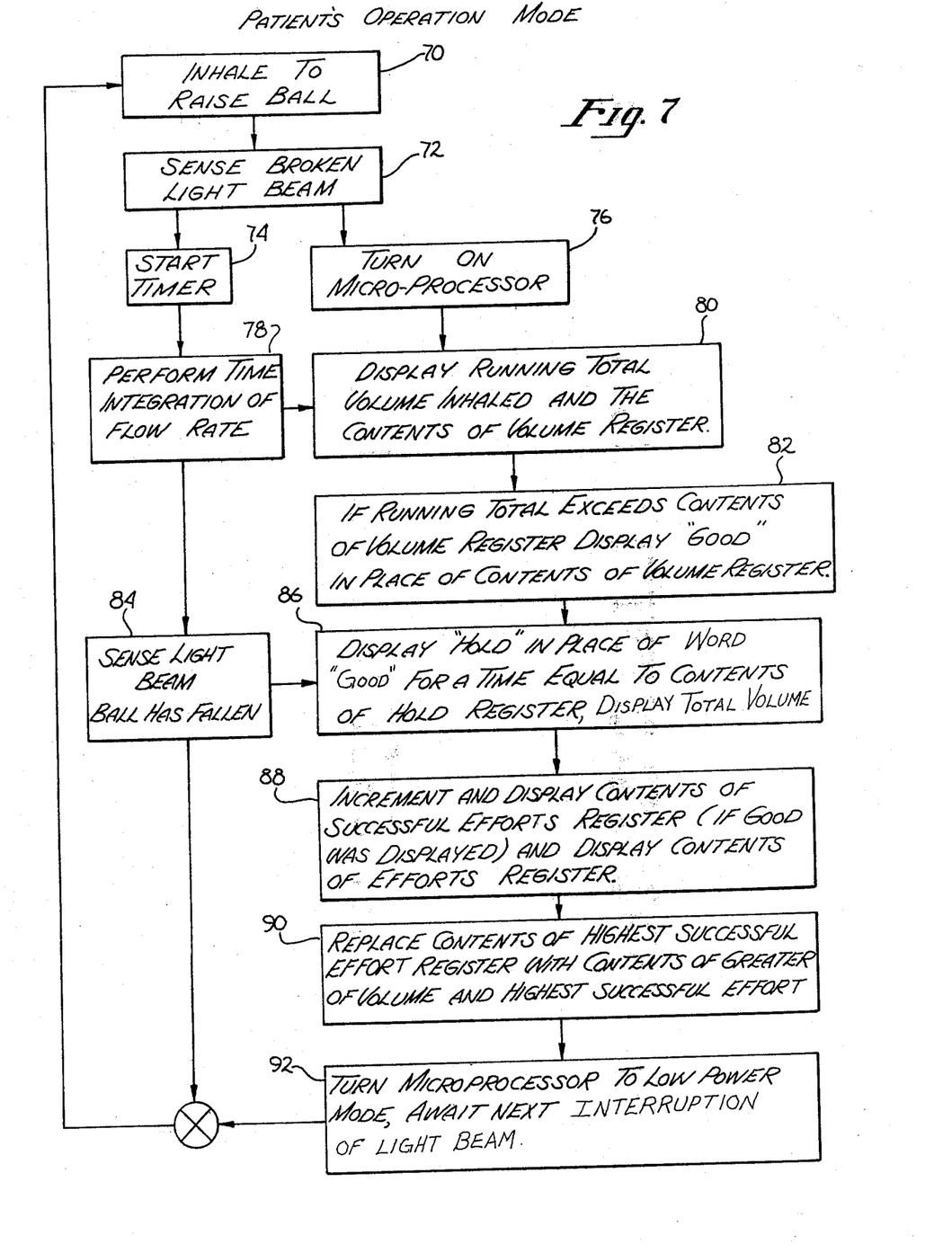
FIG. 7 is a flow chart of the patient's operation mode of the invention.

The spirometer and the device of the present invention mounted thereon are given to the patient with the counter 8 turned to the "on" state. In this condition, the energy source 30 and the energy detector 32 are communicating with one another by means of the energy beam being transmitted from the energy source 30 to the detector 32. In order to operate the device, the patient is instructed that he is to inhale on a tube 19 which is attached to the spirometer 18. This inhalation will cause the indicator 24 to rise within the chamber 22 and when the flow rate of air through chamber 22 reaches a predetermined minimum, the indicator 24 will reach the top of the chamber 22.

The patient is thus instructed to inhale to raise the indicator as shown in step 70. The indicator will rise within chamber 22 interrupting the beam of energy as indicated in step 72. This energy beam may be a light beam, a sound beam, a radio beam or any other appropriate form of energy beam which will be interrupted by the presence of indicator 24 between the energy sorce 30 and the energy detector 32. In the particular embodiment of the present invention, energy source 30 is a light source and energy detector 32 is a light detector. The indicator 24 is a ball located within the chamber 22. When the indicator 24 interrupts the beam passing from the energy source 30 to the energy detector 32, the breaking of the beam starts a timer as indicated in step 74 and the breaking of the same beam also turns on the microprocessor as shown in step 76.

In the present embodiment, the turning on of the microprocessor is not literally a turning on, but is rather a changing of the state of the microprocessor from a powered "down" state so as to consume minimum power to a power "up" state wherein the microprocessor is fully active. Further references in this discussion to turning on the microprocessor will be meant to indicate that the microprocessor changes from a powered down state to a power up state. Once the timer 102 has started and the microprocessor is in the on state, the microprocessor will perform a time integration (step 78) of the contents of the "FLOW RATE" register 106. In the present invention, this is essentially a multiplication of the flow rate as entered into the microprocessor by the therapist times the present elapsed time indicated by the timer. This running product is displayed in the left display window 14 and the contents of the "VOLUME" register is displayed in the right display window 16 as shown in step 80. When the time integration of the flow rate exceeds the contents of the "VOLUME" register 112, the right hand display window 16 will then be caused to display the word "good" in place of the contents of the "VOLUME" register. This is indicated by step 82 in FIG. 7. This display will continue for as long as the patient is able to inhale at a rate sufficient to keep the indicator at the top of the chamber 22 and maintain the energy beam in an interrupted condition.

When the indicator 24 falls from the top of the chamber 22 the energy beam will again become uninterrupted and the microprocessor will sense that the indicator 24 has left the top of the chamber 22 as shown in step 84. Once the indicator 24 has left the top of the chamber 22, the right display window 16 will display the word "HOLD" which replaces the word "GOOD" (see step 86). The left display window 14 will display the total volume inhaled prior to the ball falling. This display of the word "HOLD" will continue for a time equal to the contents of the "HOLD" register 120 which was entered by the therapist during the data entry mode. It should be noted that once the indicator leaves its position the word "HOLD" is displayed and the sequential display of calculated data proceeds. Should the patient inhale and raise the indicator in an attempt to improve his recorded performance, the present invention will not recognize the presence of the indicator until it is ready to monitor a new effort. During this time that the word "HOLD" is being displayed by the microprocessor will determine whether or not the total volume of air inhaled by the patient during the time that the indicator 24 was at the top of the chamber 22 exceeds the contents of the "VOLUME" register 112. If such is the case, the microprocessor will increment the contents of the "SUCCESSFUL EFFORTS" register 116 and display those contents in display window 14 and at the same time will display the contents of the "EFFORTS" register 118 in the right hand display window 16 (step 88). In this manner the patient will be informed as to whether or not the number of successful efforts that he has achieved is equal to the number of successful efforts which the therapist has decided is appropriate for that particular patient. If the patient during step 80 was not able to inhale the predetermined minimum volume of air required by the therapist, the word "GOOD" would not be displayed as described earlier in step 82 and the microprocessor would proceed to step 84 and 86. The microprocessor would then in step 90 compare the contents of the "HIGHEST VOLUME" register 114 with the value of the running integration of the flow rate. If the integration of the flow rate exceeded the contents of the "HIGHEST VOLUME" register 114 the contents of the "HIGHEST VOLUME" register would be replaced with the value of the time integrated flow rate. This enables the therapist to interrogate the microprocessor at a later time, and by depressing register access switch 38 access the "HIGHEST VOLUME" register 114 and determine the maximum volume of air inhaled by the patient during the previous exercise.

The microprocessor will then automatically turn itself down to a low power mode and await the next interruption of the energy beam (step 92).

Figure 8:
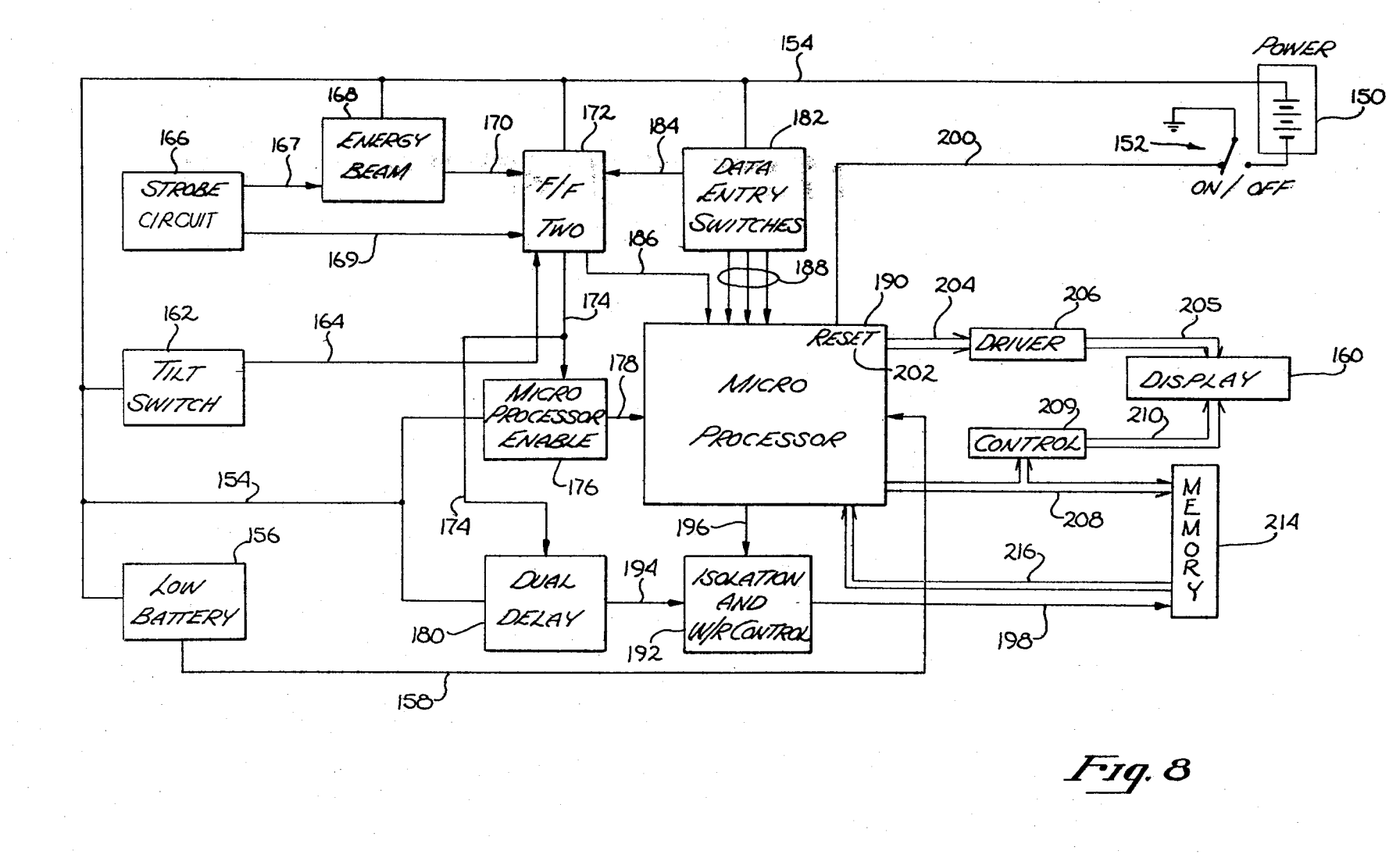
FIG. 8 is a functional block diagram of the device of the present invention.

The descriptions of FIGS. 6 and 7 were meant to be a description of the sequence of operation during the data input mode and the patient operation mode of the counter 8. FIG. 8 is intended to be the basis for a functional description of the various elements of the counter 8 of the present invention.

The counter 8 is supplied with power via a battery power supply 150. A battery charger/transformer may be used when battery power is depleted or to extend battery life when 120 v AC power is available. Power from the batteries is switched either on or off by the switch 152. The common voltage reference for the block diagram of FIG. 8 is referred to as lead 200 and is the equivalent of ground potential. While this lead is not shown as being connected to each of the various elements, it is to be understood that each of the various elements is, where appropriate, connected to a ground reference equivalent to lead 200. Power is supplied to the various elements, as appropriate, through lead 154. The block diagram of FIG. 8 is most easily understood by beginning with an explanation of the operation of the energy beam 168. It should be noted that the energy beam is not continuously "on" but rather is on only approximately 10 percent of the time. This is because the strobe circuit 166 actually pulses the energy beam at approximately 100 hertz. The energy beam is turned on for approximately one millisecond at the rate of 100 times per second. The various time lags are such, however, that the strobing of the energy beam does not activate the timer nor the microprocessor. Only a prolonged interruption, such as by the presence of the indicator 24, will cause the energy beam to be interrupted in a mode which will trigger the operation of the flip-flop circuit 172 which in turn will cause the activation of the timer and the microprocessor. The strobe 166 serves to pulse the energy beam 168 by means of a signal sent over lead 167. The strobe circuit also serves as a clock to the flip-flop circuit 172 by means of a signal which is transmitted through lead 169. It is the function of the flip-flop circuit 172 to turn on the timer and microprocessor when the appropriate logical conditions arise. The microprocessor is turned on when the energy beam is broken by the indicator 24, and when the register access switch 38 is activated. The microprocessor is turned off when the tilt switch 162 sends the appropriate signal over lead 164 to the flip-flop 172 which thereby generates a logical signal resulting in the microprocessor being turned "off". The microprocessor is also turned off a preset time after the microprocessor executes the final display instruction of the pre-programmed instructions which direct the operation of the microprocessor. When the proper logical condition exists, the flip-flop 172 will start the timer by means of a signal sent over lead 186 or will send an appropriate signal over lead 174 to the microprocessor enabling circuit 176. This microprocessor enabling circuit 176 will, after the appropriate time delay, send a signal over lead 178 which will activate the microprocessor.

This delay is one of two delays which are set by the circuitry within the dual delay block 180. This dual delay circuitry provides one delay for the turning on of the microprocessor, and another delay which keeps the microprocessor turned on for a preselected time after the execution of the last display step of the microprocessor program instructions.

When the counter is being operated in the data entry mode, the data entry switches 182 will create the appropriate logical state for the flip-flops 172 such that the operation of the data entry switches will cause the desired data to be entered over leads 188 into the microprocessor. Another input to the microprocessor comes over lead 158 from the low battery indicator 156. This circuitry is such that in the event that the power supplied over lead 154 to the low battery circuitry 156 falls below a predetermined level, the low battery indicator will send a signal to the microprocessor which causes the microprocessor to activate the display 160 so as to display a decimal point at each digit location of the display windows 14 and 16. Because the microprocessor 190 is operated in two modes, that is a low power mode and a high power mode, when the microprocessor is put into the high power mode spurious signals may be generated which, if not controlled, would interfere with the contents of the external memory 214. Such interference may result in total destruction of the contents of the memory 214. In order to avoid such destruction of the memory, there is provided an isolation and read/write control circuit 192 which in combination with the dual delay circuit 180, prevents the spurious signals from the microprocessor from interfering with the contents of the memory 214. this isolation and read/write control circuitry 192 controls the logical state of the read/write input for the external memory 214 by appropriately controlling the logical condition of the lead 198. The external memory 214 is used to store the various data, entered by the therapist, during the times that the microprocessor is in the power down condition. When the energy beam 168 is broken, the microprocessor is turned on and the contents of the external memory 214 are then transferred to the internal memory of the microprocessor for use in the processing of the various signals. Once the indicator 24 has fallen from the top of the chamber 22 the microprocessor will have calculated the various values and placed them in the appropriate registers. The display 160 which is operated under the control of the display control 209 will sequentially display in windows 14 and 16 the contents of various registers of the microprocessor. Power for the display 160 is supplied through the display drivers 206 which communicated over leads 204 to the microprocessor and through leads 205 to the various digits of the display 160. The display control 209 determines which of the various register contents will be displayed at a given time. Once the display cycle has been completed, the preprogrammed instructions for the operation of the microprocessor will reset the microprocessor including the data registers therein to await the next interruption of the energy beam 168.

Figure 9:
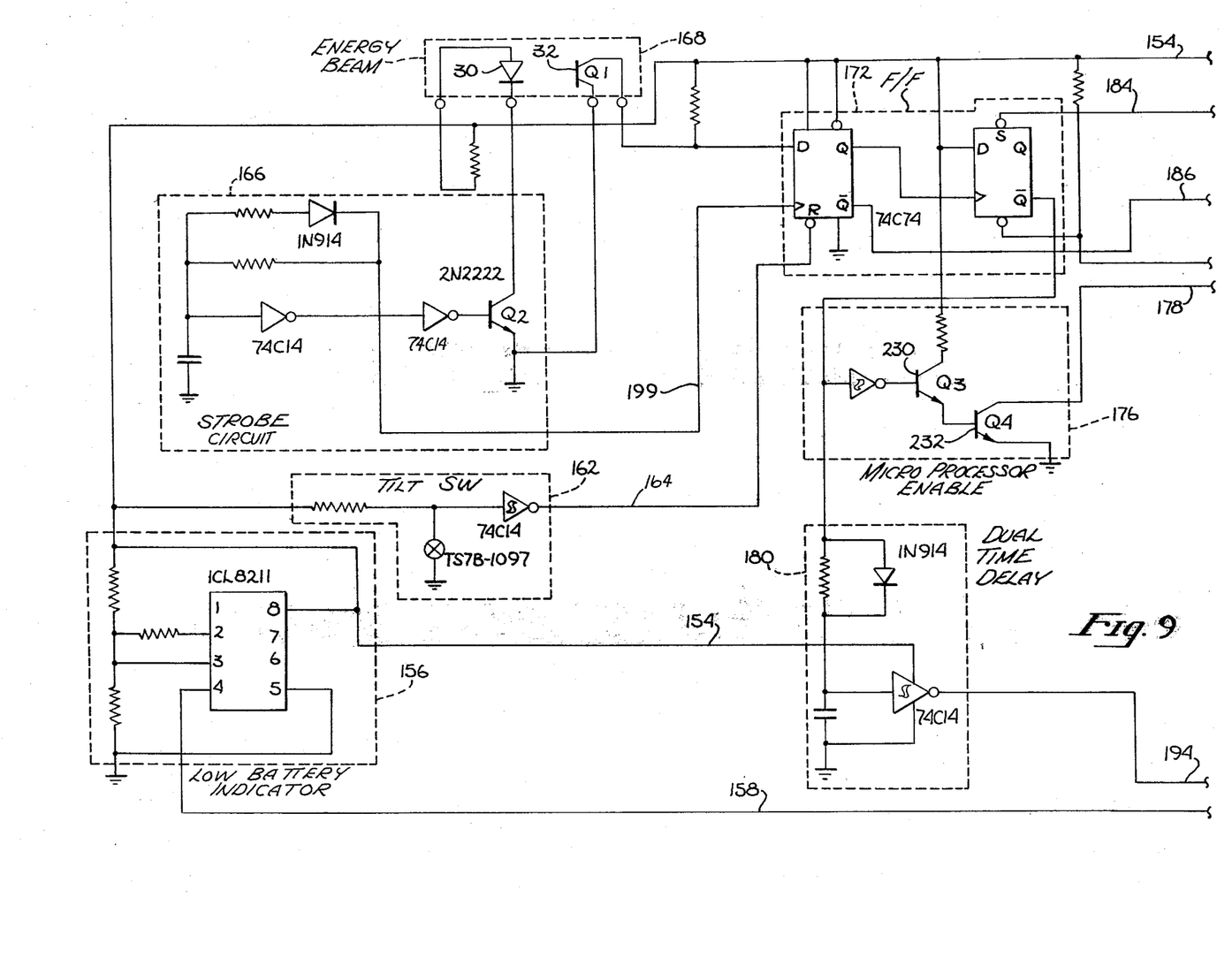
FIG. 9 is a detailed circuit diagram of a portion of the block diagram of FIG. 8.
Figure 10:
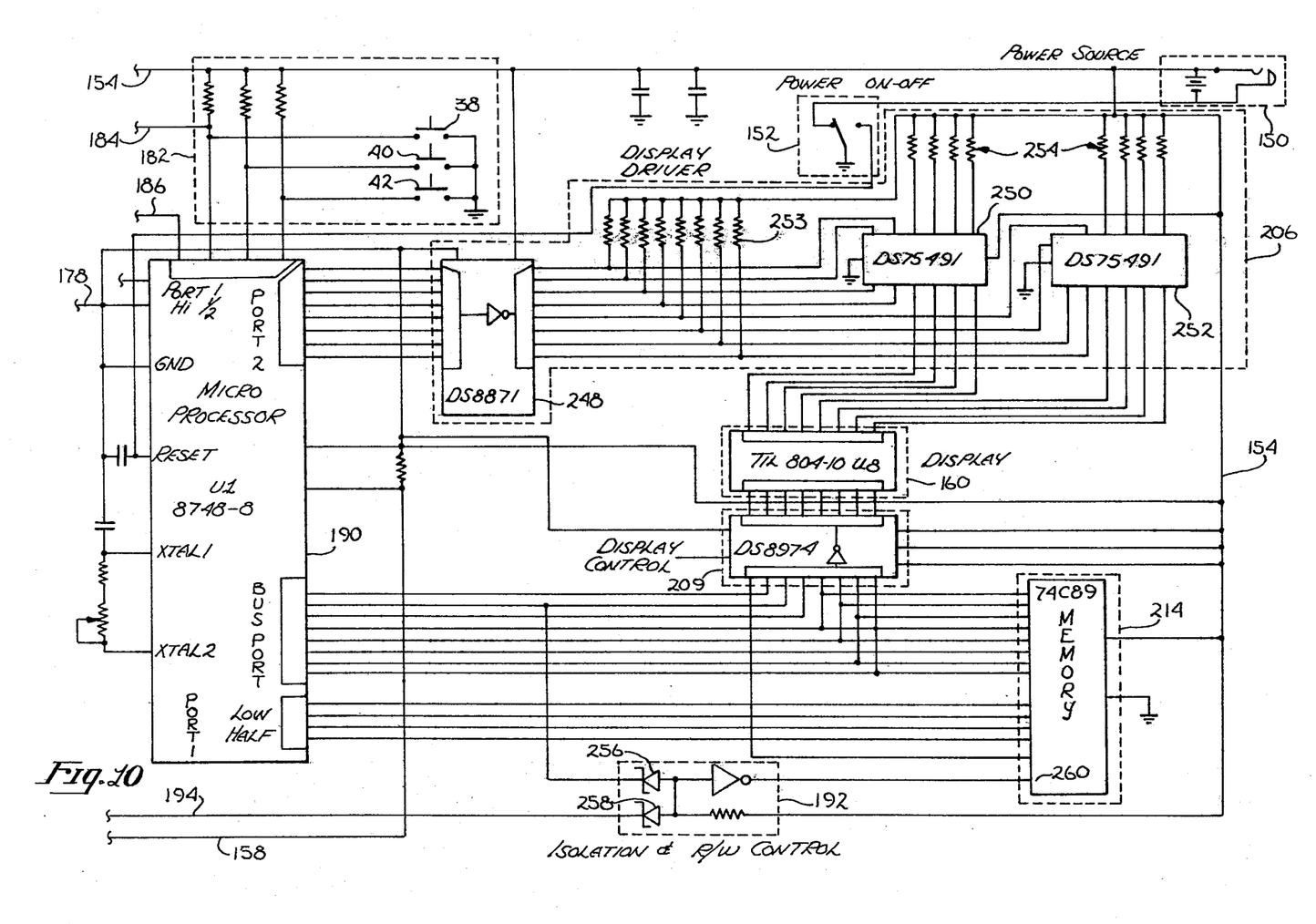
FIG. 10 is a detailed circuit diagram of the remainder of the block diagram of FIG. 8.

While this description of FIG. 8 has been in rather functional terms, the contents of the various blocks of the block diagram of FIG. 8 are more specifically illustrated in FIGS. 9 and 10. These two figures are but different portions of the block diagram of FIG. 8 with the various circuit elements within each block shown in greater detail. For example, the strobe circuit block 166 is shown in greater detail in the block labeled 166 shown in FIG. 9. The circuit elements shown within the block 166 of FIG. 9 are a particular circuit structure which will perform the functions of the strobe circuit discussed with reference to FIG. 8. Similarly, each of the blocks shown in FIG. 8 have their appropriate counterparts in either FIG. 9 or FIG. 10. The various circuit configurations shown in FIG. 9 and FIG. 10 within the different boxes are such as will accomplish the functions for those particular boxes as discussed with reference to FIG. 8. For example, the box for the display driver 206 in FIG. 8 corresponds to the circuitry shown within the box 206 of FIG. 10. The display driver 206 actually comprises three distinct driver circuits 248, 250, and 252 as well as a plurality of current limiting resistors 253 and resistors 254. These three drivers and the two series of resitors could as well be replaced by a single driver of appropriate power capacity. The microprocessor 190 shown in FIG. 8 is more particularly specified in FIG. 10 as being a microprocessor having a part no. 8748-8. This particular microprocessor chip is manufactured by Intel and is a well known device.

A more detailed explanation of the operation of the various components of the counter 8 can be made with the aid of FIGS. 9 and 10. It should be expressly understood that FIGS. 9 and 10 are meant to complement one another and the leads shown at the extreme right hand of FIG. 9 are meant to be the same as the correspondingly numbered leads shown at the extreme left hand side of FIG. 10. The detailed explanation of the operation of the device of the present invention will begin with an explanation of the strobe circuit 166.

The strobe circuit shown in block 166 of FIG. 9 will produce a signal which at the base of Q2 will alternate between a logical high state and logical low state. This will in turn cause Q2 to turn on and off thereby turning the energy source 30 on and off accordingly. When the energy source 30 is in the on condition, it will generate energy which will impact upon the energy detector 32 which in FIG. 9 is designated Q1. The oscillating signal of the strobe circuit is also used as a clock to the flip-flop circuit 172. It can be seen that when the energy beam impacts Q1, Q1 is in the "on" condition and the D input of the flip-flop 172 is tied to ground. Each time the flip-flop 172 receives the clock signal over lead 199, the output Q of the flip-flop will be in the logical low state causing the ouput $\overline{Q}$ to be in the logical high state. With $\overline{Q}$ in the logical high state, the microprocessor enabling circuit 176 is essentially turned off and the microprocessor is also therefore turned off. When the signal $\overline{Q}$ is in the logical high state, the timer is also disabled. It is therefore evident that when the indicator 24 is not located between the energy source 30 and the energy detector 32, the timer and the microprocessor are in the off condition. When the indicator 24 is between the energy souce 30 and the energy detector 32, the energy will no longer impact upon the base of the energy detector 32 (Q1) and this detector will be in the off condition. This will cause a logical high signal to appear on the D input of the flip-flop 172 and when the flip-flop is appropriately clocked by means of the strobing signal on lead 199 the output Q will be in the high condition and thus $\overline{Q}$ will be in the low condition. A low signal on $\overline{Q}$ starts the timer running and turns on Q3 and Q4 transistors causing a signal to appear on line 178 which turns the microprocessor to the on condition.

It can also be seen that should the counter 8 deviate more than a preset displacement from the vertical, the tilt switch 162 will be caused to change to the open condition thereby sending a logical low signal over lead 164 to the flip-flop 172 which causes the timer and the microprocessor to be turned to the off condition.

The low battery indicator circuit 156 compares the voltage level of the power source 150 with a pre-programmed reference power level and should the power source 150 fall below the pre-programmed level a signal will be sent over lead 158 to the microprocessor causing every digit of the display 160 to be set to a decimal point.

The dual time delay circuit 180 delays the operation of the microprocessor enable circuit 176 and in conjunction with the isolation circuit 192 thereby prevents the microprocessor 190 from generating spurious signals which would cause data to be written into the memory 214 at times which might destroy the data contents of the memory. The dual time delay 180 provides for a different time delay for turning the microprocessor on than is provided for allowing the microprocessor to turn itself off.

Referring now to FIG. 10, the isolation and read/write control circuit 192 operates in conjunction with the dual time delay 180 as previously discussed. The isolation and read/write control circuit essentially functions as a dual input NAND gate and the output of this circuit determines the logical state of the read/write control pin for the memory 214. This isolation and read/write control circuit 192 prevents the spurious output of the microprocessor, which is generated during its turn on time and turn off time, from causing erroneous writing of data into the memory 214. This isolation circuit essentially prohibits data from being written into the memory 214 until the signal into both Schottky diodes 256 and 258 is in the logical high state. Only in this condition can data be written into the memory 214. The microprocessor 190 can also be turned on by activation of switch 38 which causes the lead 184 to be tied to ground which in turn affects the flip-flop circuit 172 such that the Q output is in the logical low state thereby causing Q3 and Q4 to turn on, thus also turning on the microprocessor. Appropriate activation of the data entry switch 39 will cause the microprocessor to increment the contents of an accessed register provided switch 38 is depressed. Activation of on/off switch 41 will cause the microprocessor to clear the contents of all registers, whereas activation of clear switch 40 will clear the contents of an accessed register only.

The microprocessor 190 is controlled by and operates according to a pre-programmed set of instructions and thereby governs the functional operation of the display drivers 206, the display 160, the display control 209 and the memory 214. A representative listing of these instructions is provided in Appendix A located at the end of this specification.

Figure 11:
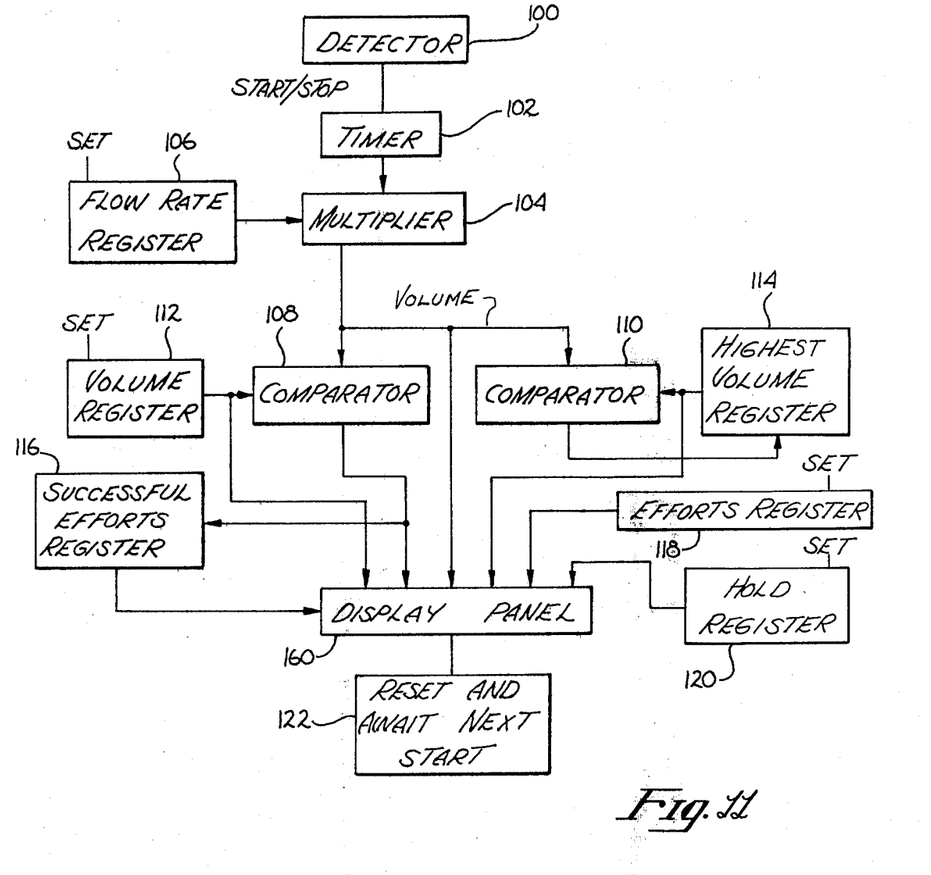
FIG. 11 is a functional block diagram of the operation of the microprocessor shown in FIG. 10.

The above referenced set of instructions may help a programmer to understand the operation of the present invention. However, a much simpler visual aid is presented in FIG. 11. With the exception of the detector 100 and the display panel 160 FIG. 11 is a functional representation of the microprocessor 190. As shown in FIG. 11 the detector 100 produces a signal which determines whether the timer 102 will start or stop and also generates a signal which will start the microprocessor. The output of the timer is used by a multiplication circuit 104 which essentially performs a time integration of the contents of the "FLOW RATE" register 106. The contents of the "FLOW RATE" register 106 have been set by the therapist prior to operation of the device by the patient. By mutiplying the output of the timer by the contents of the "FLOW RATE" register an effective time integration of the flow rate is achieved. The output of the multiplier 104 is thus a signal which is representative of the running total volume of air inspired by the patient.

This running total of the inspired volume of air is further utilized by the microprocessor to perform three operations. The first operation is performed by comparator 108 which compares the running volume of inspired air with the contents of the "VOLUME" register 112. If the comparison indicates that the time integration of flow rate exceeds the contents of the "VOLUME" register the display panel is instructed to display the word "GOOD" and the "SUCCESSFUL EFFORTS" register 116 is incremented by one indicating that the patient has successfully inhaled a volume of air exceeding that which was set by the therapist into the "VOLUME" register 112. The contents of both the "VOLUME" register 112 and the "SUCCESSFUL EFFORTS" register 116 are available for display upon demand.

The second use made of the running total of the volume of air inspired by the patient is made by the comparator 110. The running total volume of air inhaled by the patient is compared with the contents of the "HIGHEST VOLUME" register 114. The instructions of the microprocessor govern the operation of the "HIGHEST VOLUME" register and the contents of this register are representative of the highest volume of air which the patient has inspired in a given series of inhalations. If the running total volume of air inhaled by the patient exceeds the highest volume previously inspired by the patient as stored in register 114, the contents of the "HIGHEST VOLUME" register are replaced by the running total of air inspired by the patient as output by the multiplier 104. Other registers, the operation of which are governed by the microprocessor and its instructions, are the "EFFORTS" register 118 and the "HOLD" register 120. The contents of these registers have been set by the therapist prior to operation of the device by the patient. The contents of the "HIGHEST VOLUME" register 114, the "EFFORTS" register 118, and the "HOLD" register 120 are all available for display upon demand.

The third use of the output of the multiplier 104 is that of direct display. The instructions of the microprocessor direct that the running total volume of air inspired by the patient is displayed in the appropriate window on the display panel 160. After the patient can no longer maintain the minimum flow rate required to keep the indicator 24 at the top of the chamber 22, the detector 100 will generate a signal which will stop the timer 102 and begin the automatic display cycle of the microprocessor. This consists of indicating to the patient that he is to hold his breath for a predetermined time. Once the time for the patient to hold his breath has elapsed, the display will then change to indicate the number of efforts (contents of "EFFORTS" register 118) that the therapist has decided the patient is to inhale a predetermined mimimum volume of air and the display will, in addition, indicate the number of times that the patient has successfully inhaled this minimum volume of air. After a predetermined time, these displays will fade from the window and the instructions will prepare the microprocessor to reset and await the next start signal as generated by the detector 100.

Figure 12:
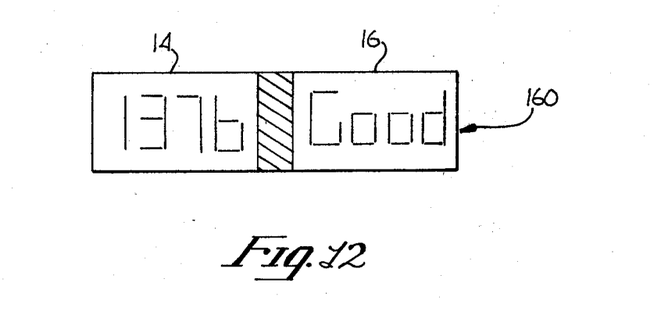
FIG. 12 is a sample of the display output.

A typical display which might be viewed by the patient is shown in FIG. 12. In window 14 is shown the volume of air that was inspired by the patient during the time that the indicator 24 was at the top of the chamber 22. In the right hand window there is displayed the word "GOOD" indicating that the volume shown in window 14 exceeds the volume programmed and entered by the therapist into the "VOLUME" register 112. The combination of the left display window 14 and the right display window 16 have been generally referred to herein as the display 160. The display 160 may comprise an appropriate array of light emitting diodes with standard electrical interconnections so as to display alphanumeric characters.

While the preceding description of the counting device of the present invention has been given with respect to some rather specific and detailed circuit diagrams, and a very specific set of microprocessor pre-programmed instructions, it should be understood that the various functions ascribed to the blocks of the various block diagrams and the various functions performed by the instructions used to govern the operation of the microprocessor could as well be performed by other circuit configurations and different pre-programmed instructions without departing from the spirit and scope of the present invention. It is believed that the ordinary worker skilled in the art would have no difficulty in making various changes and modifications in the present invention, which would not in substance change its operation. It is also believed that the ordinary skilled programmer would have no difficulty generating a set of instructions which would differ extensively from those of Appendix A, and yet would still control the microprocessor so as to function according to the invention. The scope of the present invention is believed to be broad enough to emcompass a counting device to be used in conjunction with a flow meter having an indicator which moves to a particular position indicating a predetermined rate of flow through the flow meter and the counter detecting the presence of the indicator

What is claimed is:

1. A device for use in conjunction with a flow meter having an indicator which moves to a position corresponding to the flow rate through said flow meter, said device comprising:

a housing containing a detector means, a timing means, a processing means, a first and a second storage means and an alphanumeric display means;

said first storage means for receiving and storing information representative of the minimum flow rate required through said flow meter to move said indicator to said position;

said detector means for detecting and indicating the presence of said indicator at said position;

said timing means coupled to said detector means for measuring the time during which said detector means indicates the presence of said indicator at said position;

said second storage means for receiving and storing information representative of a desired minimum volume;

said processing means coupled to said timing means and to said first storage means for generating information representative of the cumulative volume flow through said flow meter, said processing means further performing a comparison of said generated information and the information stored in said second storage means; and said alphanumeric display means coupled to said processing means for displaying an indication in the event said generated information is representative of a volume equal to or greater than the volume represented by the information stored in said second storage means.

2. A device according to claim 1 wherein said housing is provided with contours complimentary to the contours provided on said flow meter whereby said housing is removably and matably mountable upon said flow meter.

3. A device according to claim 1 wherein said detector means comprises:

an energy source for generating an energy beam;
an energy sensor for sensing said energy beam;
said energy source being spaced from said energy sensor and coupled to said energy sensor by said energy beam whereby interruption of said energy beam by said indicator passing between said energy source and said energy sensor indicates the presence of said indicator.

4. A device according to claim 3 wherein said energy source is a light source and said energy sensor is a light sensor.

5. A device according to claim 4 wherein said light source is a light emitting diode and said light sensor is a photocell.

6. A device according to claim 5 wherein said housing is provided with contours complimentary to the contours provided on said flow meter whereby said housing is removably and matably mountable upon said flow meter.

7. The device according to claim 1 wherein said display means comprises an array of light emitting diodes.

8. The device according to claim 7 wherein said housing is provided with contours complimentary to the contours provided on said flow meter whereby said housing is removably and matably mountable upon said flow meter.

9. The device according to claim 8 wherein said detector means comprises a light source and a light sensor.

10. The device according to claim 9 wherein said processing means and timing means comprises a microprocessor operating according to preprogrammed instructions.

11. A device for use in conjunction with a flow meter having an indicator which moves to a position corresponding to the flow rate through said flow meter, said device comprising:

a housing containing at least one detector means, a timing means, a plurality of data storage registers, a multiplier means, a comparator means and display means;

said detector means for detecting the presence of said indicator at said position;

said timing means coupled to said detector means for measuring the time during which said indicator remains at said position;

said plurality of data storage registers for storing data;

said multiplier means coupled to said timing means and one of said plurality of data storage registers for multiplying the output of said timing means by the contents of said data storage register;

said comparator means coupled to said data storage registers and said multiplier means for comparing the output of said multiplier means with the contents of said data storage registers and for storing the results of said comparisons in some of said data storage registers; and said display means coupled to said multiplier means, said comparator means and said data storage registers for displaying the output of the multiplier means, the results of comparisons performed by said comparator means and the contents of said data storage registers.

12. A device according to claim 11 wherein said housing and said flow meter are provided with complimentary contours whereby said housing is removably and matably mountable upon said flow meter.

13. A device according to claim 12 wherein said detector means comprises:

a light source for generating a light beam;
a light detector for detecting said light beam;
said light detector being spaced from said light source and coupled to said light source by said light beam whereby interruption of said light beam by said indicator passing between said light source and said light detector indicates the presence of said indicator.

14. A device according to claim 13 wherein said multiplier means, said comparator means, said display means, said timing means and said plurality of data storage registers comprise a microprocessor operating according to pre-programmed instructions.

15. A volume calculator and incentive display device for use with a spirometer of the type in which a movable indicator contained in a chamber moves to a certain position in said chamber only when the patient's breathing flow rate through said spirometer equals or exceeds a value set by a flow regulator control on said spirometer, said device comprising:

a case removably placeable onto said spirometer, said case including a detector housing which is situated adjacent said chamber certain position when said case is placed on said spirometer, detection means, situated in said detector housing, for detecting the presence of said indicator at said certain position and for providing an electrical detection signal in response thereto, presettable volume register means, situated in said case, for storing data representing the desired minimum volume of air to be breathed by the patient in a single breath, volume determination means, situated in said case and cooperating with said detection means, for electrically ascertaining from said detection signal the actual minimum volume of air breathed by said patient in a breath, an alphanumeric display situated on said case, and, incentive indication means, situated in said case and cooperating with said volume register means and said volume determination means, for providing on said display an incentive indication when said ascertained actual minimum volume equals or exceeds said desired minimum volume represented by said stored data.

16. A device according to claim 15 wherein said spirometer has a base and an upright region extending therefrom and including said chamber, said chamber being transparent and said indicator being opaque to light, said case having a channel conformal with said upright region for engagement therewith as said device is placed on said spirometer, said detector housing then matingly engaging said chamber certain position, said detection means including a light source and a photodetector situated within said detector housing so as to be on opposite sides of said chamber when said device is in place, light from said source illuminating said photodetector through said chamber except when interrupted by the presence of said indicator in said certain position.

17. A device according to claim 15 further comprising:

presettable flow rate register means, situated in said case, for storing data indicating the flow rate value set by said flow regulator control, said volume determination means utilizing said stored flow rate indicating data to ascertain said actual minimum volume.

18. A device according to claim 17 wherein said movable indicator moves in response to patient inhalation, said device further comprising:

"required efforts" register means for storing a number representing the desired number of times during a course of therapy that the patient is to take a breath having an actual minimum volume of air in excess of said desired minimum volume, "successful efforts" register means, cooperating with said volume determination means, for counting the actual number of times said actual minimum volume has been exceeded, "successful efforts" display means for causing the contents of said "required efforts" register means and the contents of said "successful efforts" register means to be displayed on said alphanumeric display, presettable "hold" register means for storing data representing the desired duration of time that the patient should hold his breath following each inhalation, "hold" display means, cooperating with said detection means, for causing said alphanumeric display to provide an indication that the patient should hold his breath, said indication being provided for a duration of time corresponding to that stored in said "hold" register means, said provided indication being initiated as soon as said detection means detects that said indicator is no longer present in said certain position, a set of switches mounted on said case, and data entry means, electrically connected to said switches and cooperating with said volume register means, said flow rate register means, said "required efforts" register means and said "hold" register means, for facilitating entry from said switches into the respective means of said data representing said desired minimum volume of air, said set flow rate value, said desired number of breaths and said desired duration of time.

19. A device according to claim 15 further comprising:

"required efforts" register means for storing a number representing the desired number of times during a course of therapy that the patient is to take a breath having an actual minimum volume of air in excess of said desired minimum volume, "successful efforts" register means, cooperating with said volume determination means, for counting the actual number of times said actual minimum volume has been exceeded, and "successful efforts" display means for causing the contents of said "required efforts" register means and the contents of said "successful efforts" register means to be displayed on said alphanumeric display.

20. A device according to claim 15 wherein said spirometer indicator moves in response to patient inhalation, said device further comprising:

presettable "hold" register means for storing data representing the desired duration of time that the patient should hold his breath following each inhalation, "hold" display means, cooperating with said detection means, for causing said alphanumeric display to provide an indication that the patient should hold his breath, said indication being provided for a duration of time corresponding to that stored in said "hold" register means, said provided indication being initiated as soon as said detection means detects that said indicator is no longer present in said certain position.

21. A device according to claim 15 further comprising:

highest volume register means, cooperating with said volume determination means, for storing the highest value of actual minimum volume of air breathed by said patient in any of a series of breaths the volume of which is measured by said device, and display switch means, situated on said case, for causing the value stored in said highest volume register means to be displayed on said alphanumeric display.

22. A volume calculator for use with an incentive spirometer of the type in which an indicator ball contained in a transparent column moves to the top of said column when the patient's inhalation flow rate through said spirometer equals or exceeds a value set by a flow regulator control on said spirometer, comprising:

a housing conforming in shape to said spirometer for slidingly removable mating engagement therewith, all of the following volume calculator components being contained in said housing, an alphanumeric display visible exteriorly of said housing, a set of registers, switches accessible on the exterior of said housing, and electrical means interconnected with said switches for entering into said registers data representing (a) the flow rate corresponding to that set by said flow regulator control, (b) a required minimum inhalation volume per breath, and (c) the duration of time the patient is to hold his breath upon completion of inhalation, a light source and a photodetector illuminated thereby, contained within said housing and straddling the top of said transparent column when said housing is in place on said spirometer, the presence of the indicator ball at the top of said column interrupting the illumination of said photodetector by said source, computation means, cooperating with said photodetector, for computing from the duration of time that said indicator ball is at the top of said column the actual minimum volume of air inhaled by the patient per breath and for displaying on said alphanumeric display an incentive indication when said actual volume exceeds the required minimum inhalation volume entered in said registers, hold duration means, actuated when the indicator ball falls so that said photodetector again is illuminated by said light source, for displaying on said alphanumeric display an indication that the patient should hold his breath, the duration of time of such display corresponding to said hold duration entered in said registers, maximum volume storage means, cooperating with said computation means, for storing data representing the maximum volume of air inhaled by said patient in any of a series of breaths, as determined by said computation means, counter means, cooperating with said computation means, for counting the number of times during a series of breaths that the required minimum inhalation volume has been exceeded, and readout means for displaying on said alphanumeric display said number of times counted by said counter means, and for displaying said maximum volume stored by said maximum volume storage means.

23. A device according to claim 22 wherein said incentive indication consists of the display on said alphanumeric display of a word meaning "good" and wherein said indication that the patient should hold his breath consists of the display on said alphanumeric display of a word meaning "hold".

24. A device according to claim 22 wherein said registers, said electrical means, said computation means, said hold duration means, said maximum volume storage means, said counter means and said readout means all are implemented by a microprocessor and associated memory, said microprocessor being electrically interconnected to said switches, said photodetector and said alphanumeric display and operating under the direction of a program stored in said memory.

* * * * *